United States Patent [19]

Ekiriwang et al.

[11] Patent Number: 5,948,691
[45] Date of Patent: Sep. 7, 1999

[54] CARRIER AND METHOD OF USE

[75] Inventors: James T. Ekiriwang, Plano, Tex.; Steve Herchenbach, Green Oaks; Guy Christopher Upchurch, Oak Park, both of Ill.

[73] Assignee: Abbott Laboratories, Abbott Park, Ill.

[21] Appl. No.: 09/058,630

[22] Filed: Apr. 10, 1998

[51] Int. Cl.⁶ ................................................. G01N 37/00
[52] U.S. Cl. .................. 436/183; 436/43; 422/63; 422/94; 422/104; 294/1.1; 294/27.1
[58] Field of Search ................ 436/183, 43; 422/63, 422/99, 102, 103, 104; 294/1.1, 27.1

[56] References Cited

U.S. PATENT DOCUMENTS

| | | | |
|---|---|---|---|
| 3,679,129 | 7/1972 | Livshitz et al. | 422/64 |
| 5,186,339 | 2/1993 | Heissler | 211/74 |
| 5,254,315 | 10/1993 | Nurse et al. | 422/104 |
| 5,324,481 | 6/1994 | Dunn et al. | 422/64 |
| 5,456,882 | 10/1995 | Covain | 422/64 |
| 5,525,304 | 6/1996 | Matsson et al. | 422/104 |
| 5,579,928 | 12/1996 | Anukwuem | 211/74 |
| 5,582,222 | 12/1996 | Riall | 141/346 |
| 5,700,429 | 12/1997 | Buhler et al. | 422/104 |
| 5,738,827 | 4/1998 | Marquiss | 422/104 |

FOREIGN PATENT DOCUMENTS 0 100 663  2/1984  European Pat. Off. .

*Primary Examiner*—Lowg V. Le
*Attorney, Agent, or Firm*—Mark C. Bach

[57] ABSTRACT

Embodiments of a carrier and methods of its use are disclosed. In one method, a carrier is used with a container having a positioning device to be used with a medical diagnostic analyzer having a container loading device. This method comprises releasably mating a container retaining member disposed on the carrier with the positioning device on the container. The container retaining member on the carrier is substantially aligned with the container loading device on the medical diagnostic analyzer. The container is moved from the container retaining member on the carrier to the container loading device on the medical diagnostic analyzer.

3 Claims, 5 Drawing Sheets

CARRIER AND METHOD OF USE

BACKGROUND

This case relates generally to a carrier and a method of use of that carrier. More specifically, this case relates to a carrier for a cuvette used in a medical diagnostic analyzer and a method of using such a carrier.

Medical diagnostic analyzers are machines that process a sample and determine an element of the sample. For example, a medical diagnostic analyzer may process a human blood sample and may determine an amount of cholesterol in that human blood sample.

To do this, the sample may be added to a container, such as a reaction vessel, a cuvette and the like, on the medical diagnostic analyzer. The medical diagnostic analyzer may add other things, such as reagents, etc., to the sample in the container and "look" at the container to determine the element of interest.

Some medical diagnostic analyzers can process a number, such as 250, of samples in a given time period, such as 1 hour. If one container is used for each sample processed, then the medical diagnostic analyzer needs a suitable supply of containers to do the desired processing.

In some cases, a supply of containers are loaded onto the medical diagnostic analyzer. Because the containers may be relatively small, loading of the containers onto the medical diagnostic analyzer may require some effort and time. Also, because the containers are looked at to determine the element of interest in the sample, it is desirable to keep the containers relatively clean, e.g. free of finger prints, etc. Accordingly, it is desirable to provide a carrier that may facilitate loading of containers onto an medical diagnostic analyzer, transport of containers, etc.

SUMMARY

Embodiments of a carrier and methods of its use are disclosed. In one method, a carrier is used with a container having a positioning device to be used with a medical diagnostic analyzer having a container loading device. This method comprises releasably mating a container retaining member disposed on the carrier with the positioning device on the container. The container retaining member on the carrier is substantially aligned with the container loading device on the medical diagnostic analyzer. The container is moved from the container retaining member on the carrier to the container loading device on the medical diagnostic analyzer.

DETAILED DESCRIPTION OF ILLUSTRATED EMBODIMENTS

Figure 1:
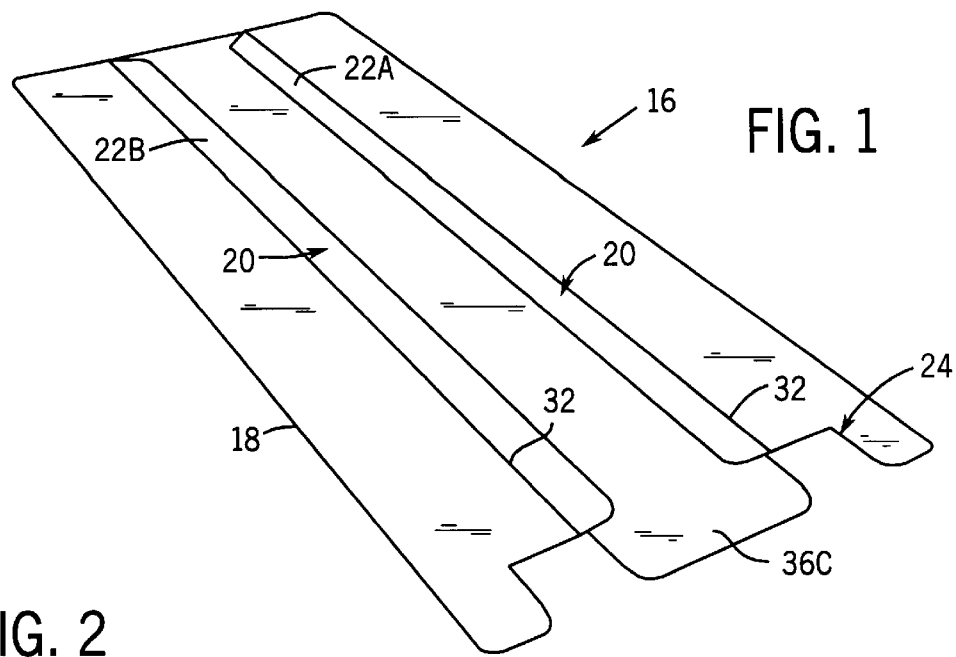
FIG. 1 is a perspective view of an embodiment of a carrier described herein.

FIG. 1 illustrates one embodiment of a carrier 16 which may be used for loading a container 1 onto an instrument, such as a medical diagnostic analyzer and the like. For the sake of clarity of understanding, construction, operation and use of the carrier 16 are discussed hereinbelow with respect to the container 1 and the medical diagnostic analyzer described in U.S. Pat. No. 5,456,882 and European Patents No.'s EP 0 557 400 B1 and EP 0 557 403 B1. Those patents are assigned to the assignee of the present case and the disclosures thereof are incorporated herein in their entirety by this reference. To further facilitate understanding, reference characters in this case are preserved from the '882 patent referenced above. However, it is to be recognized that the carrier 16 may be utilized with other containers and other methods of use. Additionally, steps comprising methods of construction and/or methods of use of the carrier 16 may be performed in any appropriate manner and may be combined with steps of other methods to arrive at yet additional methods.

Referring to FIG. 1, the carrier 16 generally comprises a substantially planar member 18 including a container 1 retaining member 20 disposed on the planar member 18. The container 1 retaining member 20 has a configuration which is matable with the positioning device 6 on the container 1 such that the container 1 is releasably retained with the carrier 16 and such that the carrier 16 is releasably engagable with the positioning device 6 on the container 1 such that the container 1 can be releasably or slidably retained with the carrier 16. In the illustrated embodiment, the container retaining member 20 comprises at least one flap, i.e. a pair of opposed flaps 22A and 22B configured for removable insertion into grooves 10 on the positioning device 6 of the container 1. Other constructions of the container 1 retaining member 20 are also possible depending upon the construction of the positioning device 6.

Figure 7:
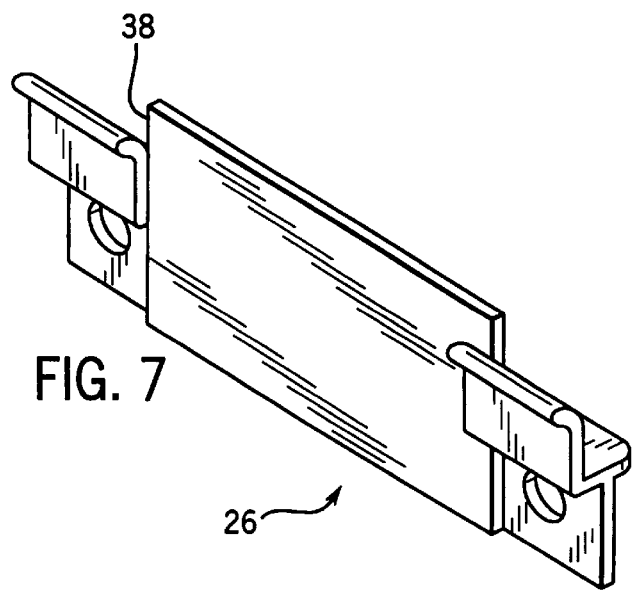
FIG. 7 is a perspective view of the mating portion of the medical diagnostic analyzer of FIG. 6 mated with the carrier of FIG. 1.
Figure 8:
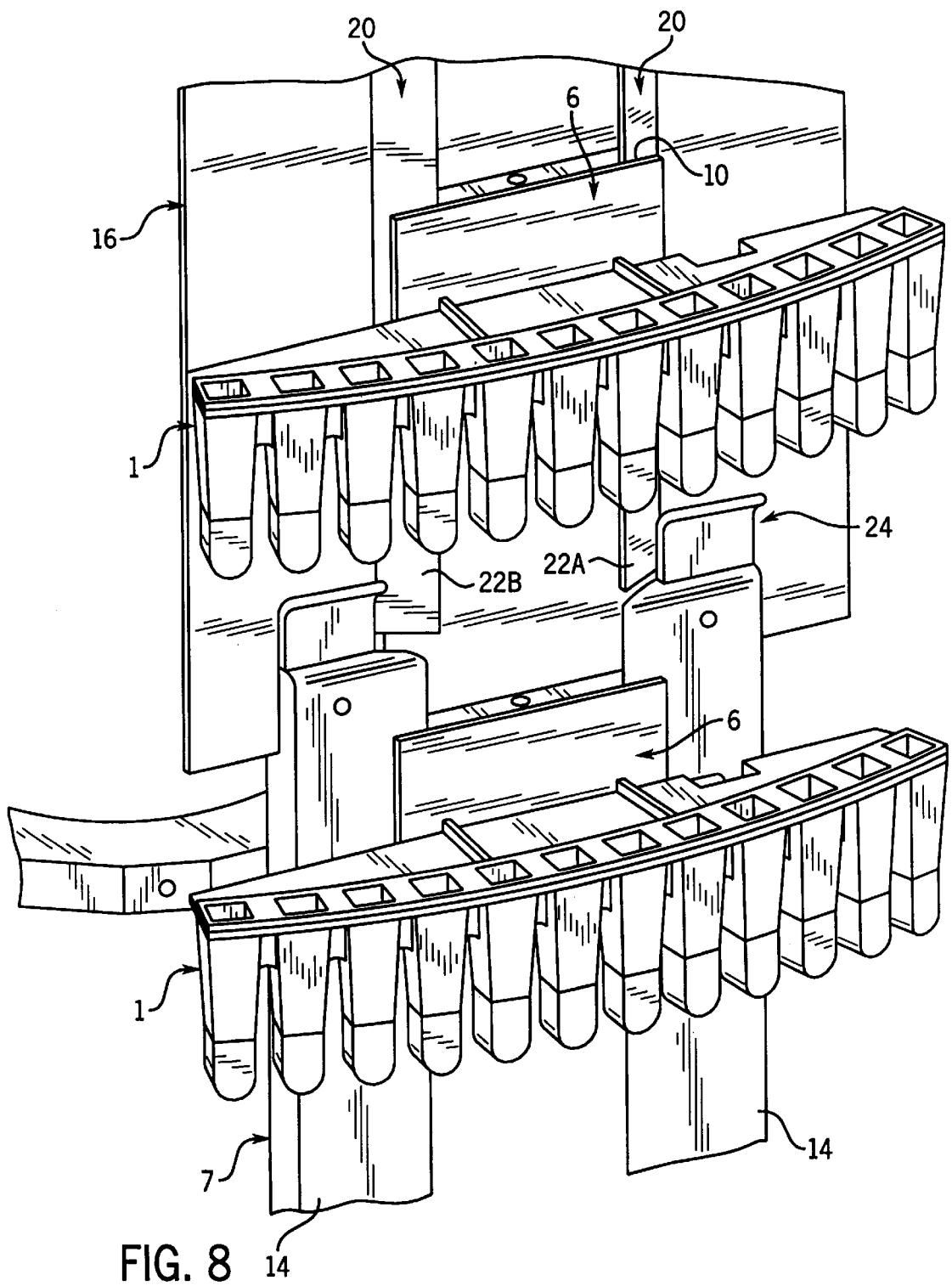
FIG. 8 is a perspective view, similar to that of FIG. 6, illustrating loading of containers onto the medical diagnostic analyzer with aid of the carrier of FIG. 1.

The carrier 16 also includes an instrument engaging portion 24 which releasably mates with a mounting element 26 (FIG. 7) located on a machine, such as an automatic medical diagnostic analyzer and the like, which utilizes the container 1. The illustrated embodiment of the carrier 16 is dimensioned such that a plurality, such as about 8 containers 1, may be disposed on the carrier 16 in intended fashion at any given time.

Further details of the carrier 16 may be appreciated upon review of the following discussion of an exemplary method of construction of one embodiment of the carrier 16. It is to be noted that other methods of construction are also possible. Furthermore, while particular exemplary materials and dimensions may be listed, other materials and dimensions may be used as appropriate.

Figure 2:
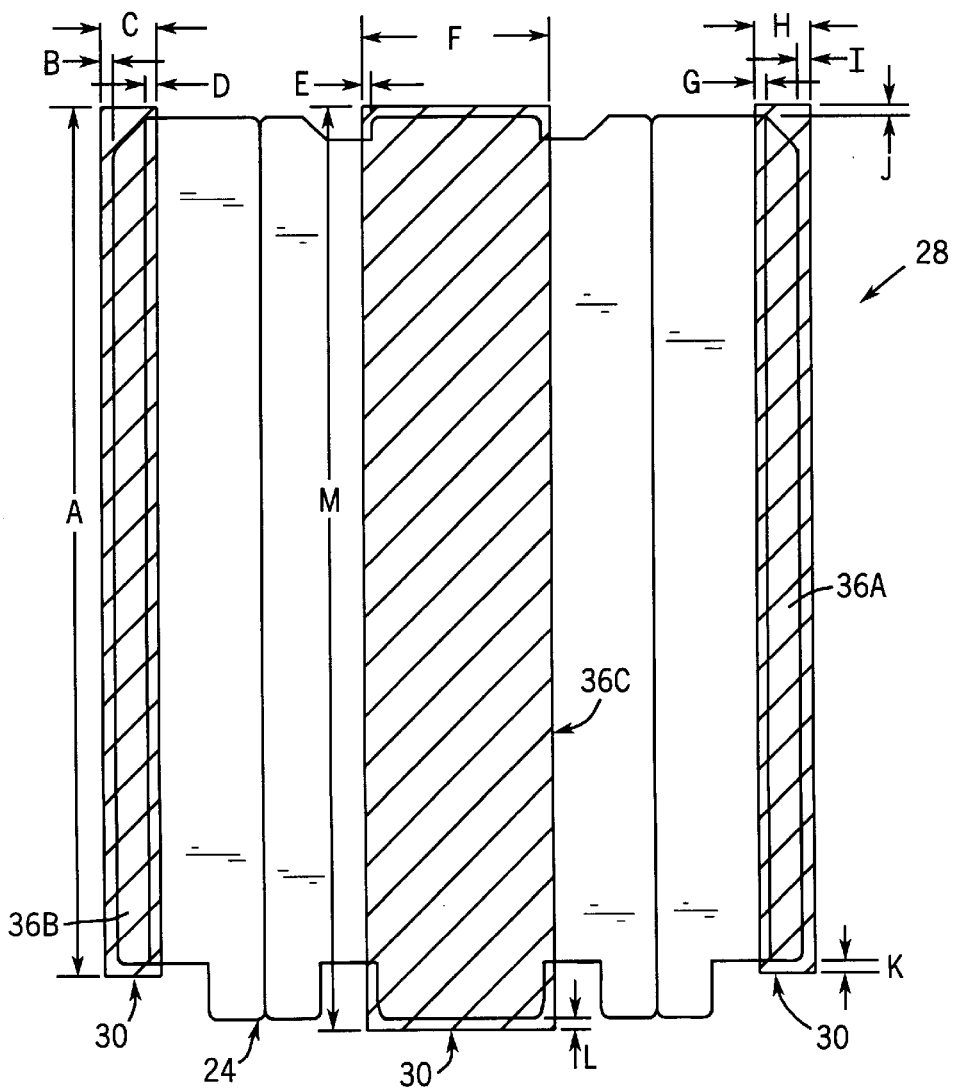
FIG. 2 is a generic elevational view of a blank being constructed into the carrier of FIG. 1.

Construction of the carrier 16 can begin with a suitable raw material, such as a card stock and the like. In one embodiment, the raw material may be an approximately 0.016 inch thick solid bleached sulfate paper board, such as 16PT EVEREST FC8 NEW SHADE available from International Paper of Memphis, Tenn., having at least one clay coated side and one uncoated side. The raw material is cut to form a blank 28 having a configuration shown in FIG. 2. In one embodiment, the blank 28 may have approximately the following dimensions.

| REFERENCE | DIMENSION |
|---|---|
| A | 9 7/8" |
| B | 1/8" |
| C | 5/8" |
| D | 1/8" |
| E | 1/8" |
| F | 2 1/16" |
| G | 1/8" |
| H | 5/8" |
| I | 1/8" |
| J | 1/8" |
| K | 1/8" |
| L | 1/8" |
| M | 10 1/2" |

The blank 28 may then be subjected to a coating procedure, such as a print press run and the like. In one method, this coating procedure comprises adding a spot of an aqueous coating, such as Nicoat work-in-turn gloss coating, formula #89100, available from Nicoat of Bensenville, Ill., to at least portions of at least one side of the blank 28. In one embodiment, this coating may be disposed on a clay coated side of the blank 28. An area occupied by the coating is indicated by reference character 30 on FIG. 2. Dimensions B and I represent "bleed" areas of the coating.

Figure 3:
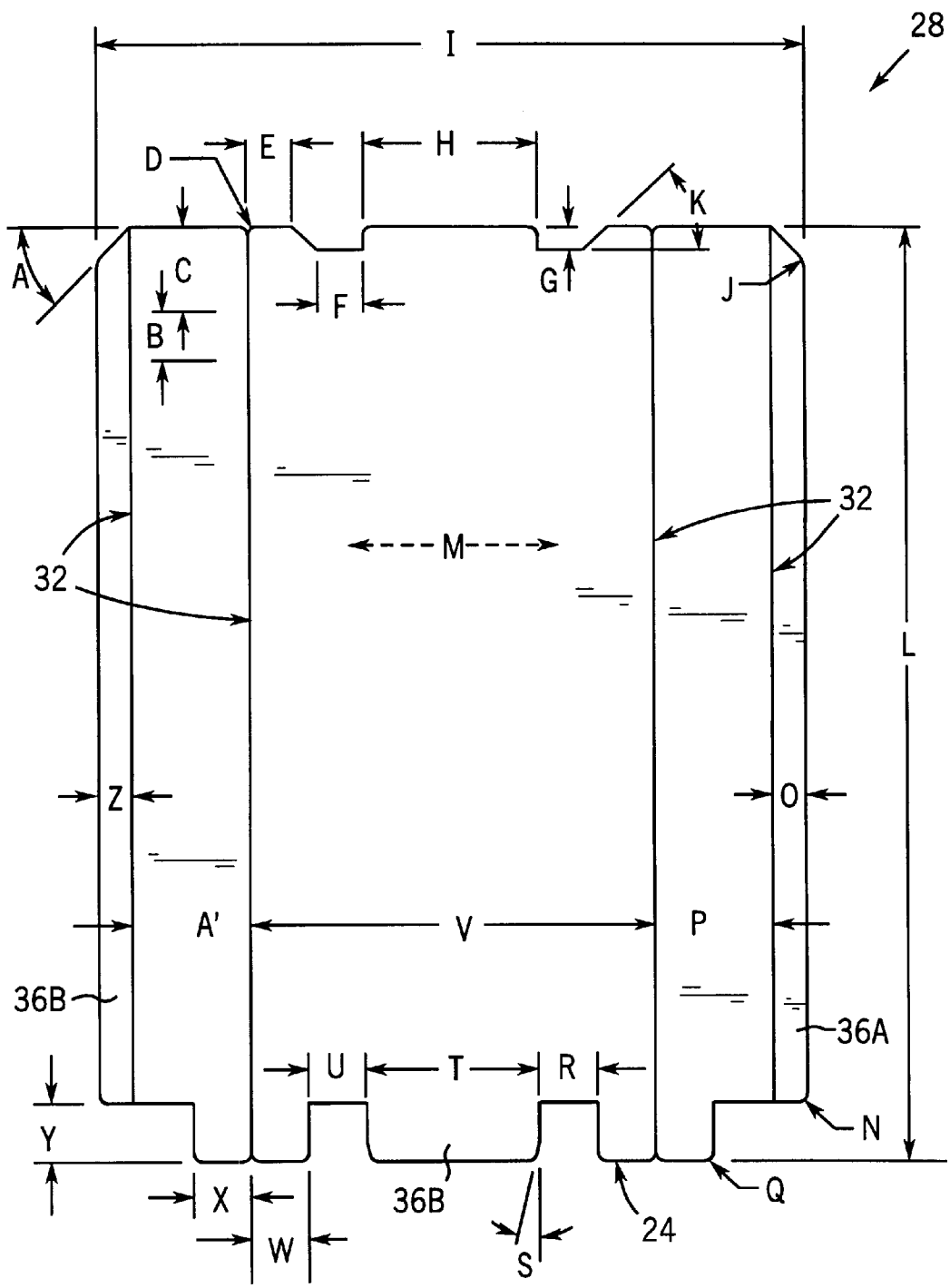
FIG. 3 is another generic elevational view of a blank being constructed into the carrier of FIG. 1.

Next, the blank 28 is fabricated into a configuration illustrated in FIG. 3. Specifically, the blank 28 may be cut, e.g. die cut, crimped, perforated, creased, scored and/or embossed as appropriate. The blank 28 now may have approximately the following dimensions.

| REFERENCE | DIMENSION |
|---|---|
| A | 45 degrees |
| B | 1/2" |
| C | 7/8" |
| D | 1/8" radius |
| E | 1/2" |
| F | 1/2" |
| G | 1/4" |
| H | 1 13/16" |
| I | 7 17/32" |
| J | 1/4" radius |
| K | 45 degrees |
| L | 10 1/4" |
| M | Grain |
| N | 1/8" radius |
| O | 3/8" |
| P | 1 15/64" |
| Q | 1/8" radius |
| R | 11/16" |
| S | 15 degrees |
| T | 1 3/4" |
| U | 11/16" |
| V | 4 5/16" |
| W | 19/32" |
| X | 19/32" |
| Y | 5/8" |
| Z | 1 15/64" |
| A' | 3/8" |

In an exemplary embodiment, the blank 28 may be subjected to a process known to those skilled in the relevant art as "perf-in-channel" or "cut-in-crease" to form alternating scores, perforations and/or creases to facilitate further construction of the carrier 16. That process may produce, among other things, at least one arrangement of cuts and creases on the blank 28. In the illustrated embodiment, the arrangement is indicated by reference character 32 and may comprise four substantially linear segments consisting of alternating cuts and creases, each being about 0.5" in length.

Figure 4:
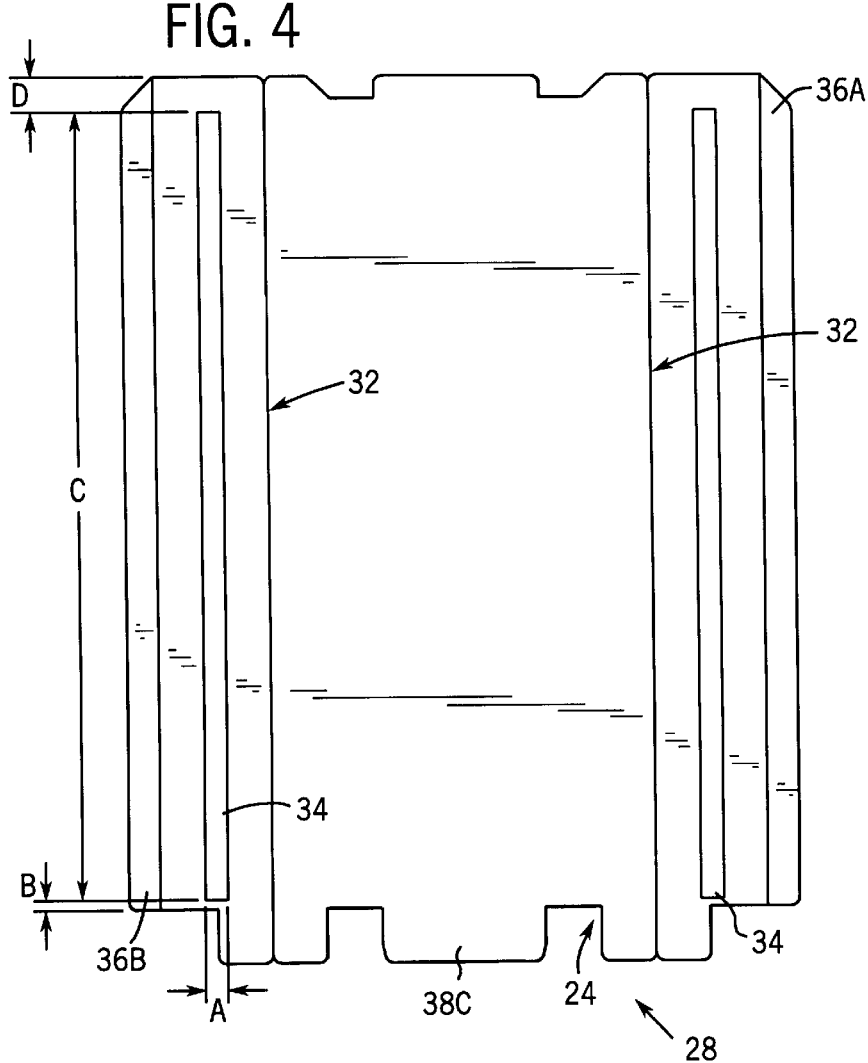
FIG. 4 is an additional generic elevational view of a blank being constructed into the carrier of FIG. 1.

Now, an adhesive 34 may be applied to the blank 28, as shown in FIG. 4. The adhesive 34 may be Resyn 33-9159 available from National Starch and Chemical of Bridgewater, N.J. Reference may be had to U.S. Pat. No. 5,100,944 for further details regarding the adhesive 34. The adhesive 34 may be applied by a suitable machine, such as a Mactron computerized gluing system available from Mactron of Alsip, Ill. in a "cold" state to form a number, such as two, of lines on the blank 28. Locations and dimensions of the adhesive 34 on the blank 28 have been empirically determined such that the carrier 16 retains the container(s) 1 in the desired manner, i.e. the flaps 22A and 22B remain sufficiently flexible. The blank 28 has the following approximate dimensions.

| REFERENCE | DIMENSION |
|---|---|
| A | 1/4" |
| B | 1/8" |
| C | 9 1/8" |
| D | 3/8" |

Figure 5:
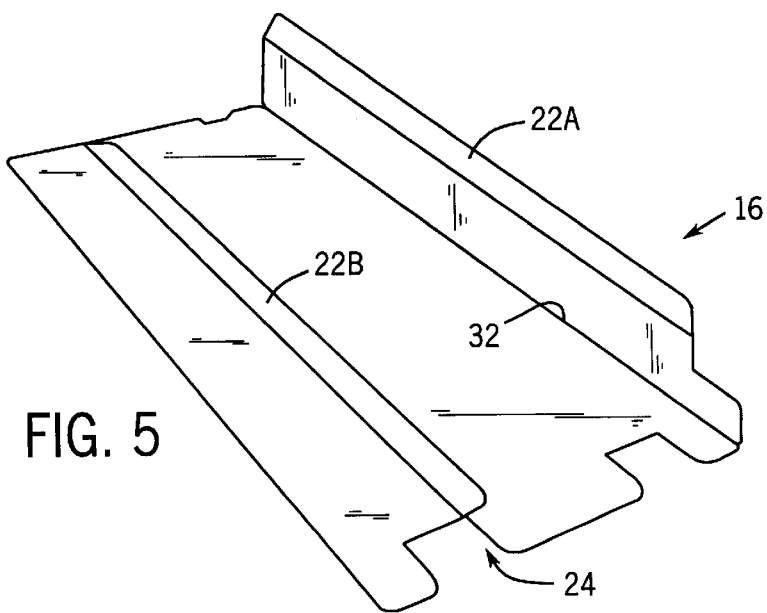
FIG. 5 is a perspective view of a blank being constructed into the carrier of FIG. 1.

With the adhesive 34 applied, the blank 28 is ready for formation into the carrier 16. Portions of the blank 28 are folded along the cuts and creases 32 previously formed. In one embodiment, portions of the blank 28 are folded at an angle of about 180 degrees, as shown in FIG. 5, such that the adhesive 34 contacts an opposing portion of the blank 28. In an exemplary embodiment, this folding brings the adhesive 34 into contact with a clay coated side of the planar member 18. Upon folding, the folded blank 28 is sufficiently compressed to provide adequate bonding of the adhesive 34 to hold the opposed portions of the blank 28 together. Also, the flaps 22A and 22B are offset from other portions of the blank 28 such that the positioning device 6 on the container 1 is slidably positionable and releasably retained with respect to the carrier 16.

With the carrier 16 being thusly constructed, a plurality, such as 8, containers 1 can be loaded on to the carrier 16. To do this, the grooves 10 on the positioning devices 6 on the containers 1 are substantially aligned with the flaps 22A and 22B on the carrier 16. The containers 1 and the carrier 16 are moved with respect to each other such that the flaps 22A and 22B are inserted into the grooves 10 on the positioning devices 6. The carrier 16, and specifically the flaps 22A and 22B are constructed such that the flaps 22A and 22B are slidable within the grooves 10.

This sliding movement is also facilitated by the lubricious coating 30 on the carrier 16. It is to be remembered that, given the manner in which the carrier 16 was constructed, e.g. the folds, the coating 30 is present on container 1 engaging surfaces 36A and 36B, disposed on the flaps 22A and 22B, and 36C disposed between the flaps 22A and 22B. The coating 30 provides a lubricious layer or surface to promote movement of containers 1 with respect to the carrier 16. Of course, the coating 30 may be replaced with any other suitable coating to meet given requirements. Also, the carrier 16 is constructed such that optical surfaces of the containers 1 are not in contact with surfaces or other things, i.e. particulate and the like, that might adversely effect desired properties, such as light transmittance, etc., of those optical surfaces.

In some instances, once the containers 1 have been joined with the carrier 16, the combination of the containers 1 and the carrier 16 may be wrapped with a suitable material, such as a sheet of a suitable polymer and the like. These wrapped carriers 16 may be transported in appropriate transport items, such as boxes.

Further advantages of the carrier 16 may become evident with reference to the following discussion of use of the carrier 16 bearing a plurality of containers 1.

Figure 6:
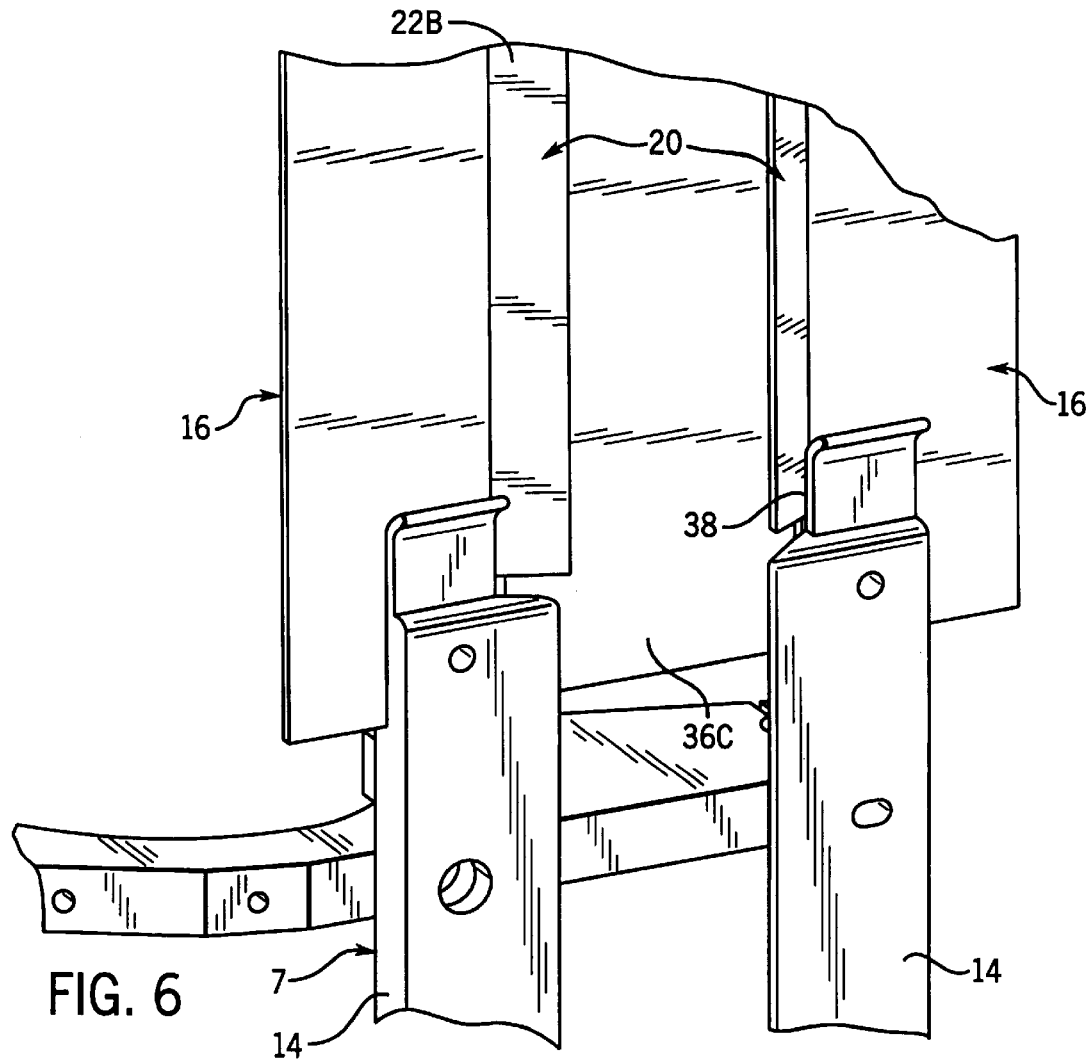
FIG. 6 is a perspective view of the carrier of FIG. 1 joined with one embodiment of a mating portion of a medical diagnostic analyzer.

If the carrier 16 is wrapped, the wrapping material is removed and may be discarded. In one utilization, the carrier 16 is positioned with respect to a mounting element 26 (FIG. 7) fixed to the vertical guides 14 on the instrument, as shown in FIG. 6. In detail, the instrument engaging portion 24 of the carrier 16 is removably inserted into a slot 38 formed on the mounting element 26. The mounting element 26 is constructed such that, upon insertion of the instrument engaging portion 24 into the mounting element 26, the flaps 22A and 22B of the carrier 16 are substantially aligned with the vertical guides 14 of the loading device 14 such that the grooves 10 of the positioning device 6 on the containers 1 are also substantially aligned with the vertical guides 14 of the loading device 7. With this positioning, it is possible for an operator to move the containers 1, either one at a time or in groups, from the carrier 16 to the vertical guides 14 of the loading device 7.

Once all or a desired number of the containers 1 have been moved from the carrier 16 to the loading device 7, the operator can remove the carrier 16 from the mounting element 26. Of course, the carrier 16 may be removed from the mounting element 26 at any time.

The instrument may include an unloading device which is constructed substantially identically to the loading device 7, i.e. the unloading device may include substantially similar vertical guides. In this case, once the medical diagnostic analyzer is finished with a container 1, the container 1 may be disposed on vertical guides comprising the unloading device. Because the unloading device is substantially identical to the loading device 7, the carrier 16 may be connected with a mounting element 26 on the unloading device. Thus, containers 1 on the unloading device may be transferred to the carrier 16 after use of the containers 1 by the medical diagnostic analyzer.

What is claimed is:

1. A method of using a carrier for a container having a positioning device to be used with a medical diagnostic analyzer having a container loading device, the method comprising the steps of:

(a) releasably mating a container retaining member disposed on the carrier with the positioning device on the container;

(b) substantially aligning the container retaining member on the carrier with the container loading device on the medical diagnostic analyzer; and (c) moving the container from the container retaining member on the carrier to the container loading device on the medical diagnostic analyzer.

2. A method as defined in claim 1 further comprising the step of:

(c) releasably mating a medical diagnostic analyzer engaging portion on the carrier with a mounting element on the medical diagnostic analyzer.

3. A method as defined in claim 1 further comprising the step of:

(c) moving the container from an unloading device on the medical diagnostic analyzer to the container retaining member on the carrier.

\* \* \* \* \*